United States Patent
Furusawa et al.

(10) Patent No.: US 6,790,175 B1
(45) Date of Patent: Sep. 14, 2004

(54) ENDOSCOPE SYSTEM

(75) Inventors: Koichi Furusawa, Tokyo (JP); Masaru Eguchi, Tokyo (JP); Tetsuya Utsui, Saitama-ken (JP); Tetsuya Nakamura, Saitama-ken (JP); Ryo Ozawa, Tokyo (JP); Shinsuke Okada, Saitama-ken (JP)

(73) Assignee: PENTAX Corporation, Tokyo (JP)

( * ) Notice: Subject to any disclaimer, the term of this patent is extended or adjusted under 35 U.S.C. 154(b) by 278 days.

(21) Appl. No.: 09/696,178

(22) Filed: Oct. 26, 2000

(30) Foreign Application Priority Data

Oct. 28, 1999 (JP) .......................................... 11-306441

(51) Int. Cl.[7] .............................................. A61B 1/00
(52) U.S. Cl. ....................... 600/128; 600/129; 600/130
(58) Field of Search ................................ 600/101, 109, 600/118, 126, 130, 166, 178, 181, 182, 247, 249, 407, 976, 160, 467, 476

(56) References Cited

U.S. PATENT DOCUMENTS

| 6,099,466 A | 8/2000 | Sano et al. ................. 600/160 |
| 6,370,422 B1 * | 4/2002 | Richards-Kortum et al. .......................... 600/478 |
| 6,485,413 B1 * | 11/2002 | Boppart et al. ............. 600/160 |

FOREIGN PATENT DOCUMENTS

JP  5-130995  5/1993

* cited by examiner

Primary Examiner—Marvin F. Lateef
Assistant Examiner—John R Sanders
(74) Attorney, Agent, or Firm—Greenblum & Bernstein, P.L.C.

(57) ABSTRACT

An endoscope system is provided with a light guide including a plurality of optical paths, and a low-coherent light source that emits a low-coherent light beams. The low-coherent light source is provided at a proximal end side of the light guide. The light beams emitted by the low-coherent light source are incident on the plurality of optical paths, respectively. The endoscope system is further provided with an interferometer unit. The interferometer unit includes a beam splitting element that splits each of the low-coherent beams emitted from the distal end of the light guide and emits split one of each of the beams to an object, a reference optical system that guides the other split beam of each of the beams, a reflector unit that reflects the beams guided by the reference optical system toward the beam splitting element, and a light detecting device that detects an interfered beam generated by interference, at the beam splitting element, between the beam reflected by the object and the beam reflected by the reflector unit. The endoscope system is further provided with a driving unit that moves the interferometer unit toward/away from the object, and a signal processing system that generates a tomogram based on signals detected by the light detecting device.

11 Claims, 8 Drawing Sheets

ENDOSCOPE SYSTEM

BACKGROUND OF THE INVENTION

The present invention relates to an endoscope system that is capable of capturing in vivo OCT (Optical Coherence Tomography) images of an object.

Conventionally, endoscope systems for observing objects inside a human cavity have been known. Such an endoscope system is provided with an endoscope, which is to be inserted inside the human cavity, and an illuminative external device, which is to be connected to the endoscope. The external device includes a light source unit for illuminating the object and a processor for processing image signals.

The endoscope includes:
- an illuminating optical system, which is connected to the light source unit of the external device and used for illuminating an object (e.g., the paries of a body cavity);
- an objective optical system for forming an optical image of the object; and
- a CCD (Charge Coupled Device) provided substantially at a focal plane of the objective optical system and electrically connected to the processor of the external device.

At a tip end of the endoscope, an instrument opening is formed. Forceps or various kinds of treatment instruments inserted in the endoscope are protruded from the instrument opening inside the human cavity.

With the endoscope system described above, an operator is capable of observing inside the human cavity. The operator firstly inserts the endoscope inside the human cavity. Light emitted by the light source unit of the external device is projected to an object to be observed through the illuminating optical system. An optical image of the illuminated object is formed, through the objective optical system, on the light receiving surface of the CCD. The CCD converts the received optical image into an electronic image (i.e., image signal), which is transmitted to the processor of the external device. The processor processes the received image signal, and displays the image of the object on a displaying device. Thus, the operator is capable of observing inside the human cavity of a patient through the displaying device.

If the operator judges that there is a possibility of a cancer or a tumor within the observing portion of the human cavity, a forceps or biopsy instrument is inserted in an instrument channel inside the endoscope. The tip portion of the instrument is protruded from the instrument opening, and the tissues of the portion in question are collected. The tissues thus obtained is subjected to a pathological inspection, and based on the results of the inspection, diagnosis is made.

According to the conventional endoscope system as described above, only the surface of the human cavity is observable. In order to know the condition of tissues beneath the paries of the human cavity, biopsy operation is required. In particular, in order to find an early cancer or a small tumor, the biopsy operation is indispensable. However, the pathological inspection requires time, and therefore, the diagnosis requires relatively long time.

Further, in view of a burden to the patient, the biopsy can be done only in a limited area and by a limited number of times. Diseased portion may be present at a portion other than the portion identified by the operator. However, such a portion might be overlooked, and as a result, an accurate diagnosis may not be done even if the pathological inspection is performed.

SUMMARY OF THE INVENTIONS

It is therefore an object of the present invention to provide an improved endoscope system that enables an accurate diagnosis within a relatively short period of time.

For the object, according to the present invention, there is provided an endoscope system, which is provided with a light guide including a plurality of optical paths, a low-coherent light source that emits low-coherent light beams, the low-coherent light source being provided at a proximal end side of the light guide, the light beams emitted by the low-coherent light source being incident on the plurality of optical paths, respectively. The endoscope system is further provided with an interferometer unit having a beam splitting element that splits each of the low-coherent light beams emitted from the distal end of the light guide and emits split one of each of the beams to an object, a reference optical system that guides the other split beam of each of the beams, a reflector unit that reflects the beams guided by the reference optical system toward the beam splitting element, and a light detecting device that detects an interfered beam generated by interference, at the beam splitting element, between the beam reflected by the object and the beam reflected by the reflector unit. The endoscope system is further provided with a driving unit that moves the interferometer unit toward/away from the object, and a signal processing system that generates a tomogram based on the signal detected by the light detecting device.

In such an endoscope system, the driving unit moves the interferometer unit toward/away from the object, that is, the interferometer unit scans the object, in the direction of the depth of the object, and the signal processing system generates a tomogram based on the signal detected by said light detecting device.

Optionally, the reference optical system includes an optical member having a relatively high refractive index. Preferably, the optical member is formed with a non-reflecting surface against the range of wavelength of the low-coherent light beams on the beam splitting element side, and a reflecting surface on the other side.

Alternatively, the reference optical system may have a gradient index optical member whose refractive index is greater at a portion closer to the reflector unit, and smaller at a portion farther from the reflector unit.

In this case, it is preferable that, the refractive index of the gradient index optical member, at abeam splitting element side, has substantially the same refractive index as the beam splitting element.

Still optionally, the interferometer unit is accommodated in the distal end portion of the endoscope.

Further optionally, the driving unit may include a driving force supply that is provided at the proximal end side of the endoscope and supplies driving force, and a force transmitting member that is connected to the driving force supply and the interferometer unit, the force transmitting member transmitting the force supplied by the driving force supply and moves the interferometer unit.

Further optionally, the light guide may be composed of a fiber array having a plurality of single-mode optical fibers arranged in parallel. Optionally, each single-mode optical fibers preserves its polarization.

Optionally, the beam splitting element is a beam splitter prism or an optical fiber coupler.

In this case, the endoscope system may further include a collimating lens array that is formed with a plurality of lens surfaces that collimates each of the beams emitted from the fiber array into parallel light beam, each of the parallel light beams being directed toward the beam splitting element, and a collective lens array including a plurality of lens surfaces that converges one of the parallel beams split by the beam splitting element on the object.

Still optionally, the low-coherent light source may include a super-luminous diode.

Yet optionally, the endoscope system may include an illuminating optical system that emits at least one of visible light, and excitation light which causes biotissues to fluoresce, toward the object, an objective optical system that converges the light from the surface of the object to form an object image; and an image capturing system that captures the optical image formed by the objective optical system.

In this case, the endoscope system may include a visible light source that emits visible light, an excitation light source that emits the excitation light, and a light source switching system that causes one of the visible light and the excitation light to be incident on the illuminating optical system. The objective optical system may form a normal light image of the object when the visible light is incident on the illuminating optical system, and the objective optical system may form a fluorescent light image of the object when the excitation light is incident on the illuminating optical system.

Still optionally, the endoscope system may include a displaying device that displays the object image captured by the image capturing system, and the tomogram generated by the signal processing system. Preferably, the normal light image, the fluorescent light image and the tomogram may be displayed at the same time at different displaying areas defined on the displaying device.

DESCRIPTION OF THE ACCOMPANYING DRAWINGS

FIG. 1 is a block diagram schematically illustrating an electrical structure of an endoscope system according to an embodiment of the invention;

FIG. 2 schematically shows optical paths of an OCT unit;

FIG. 3 schematically shows optical paths of the OCT unit, which has been moved closer to the object than the OCT unit shown in FIG. 2;

Figure 4:
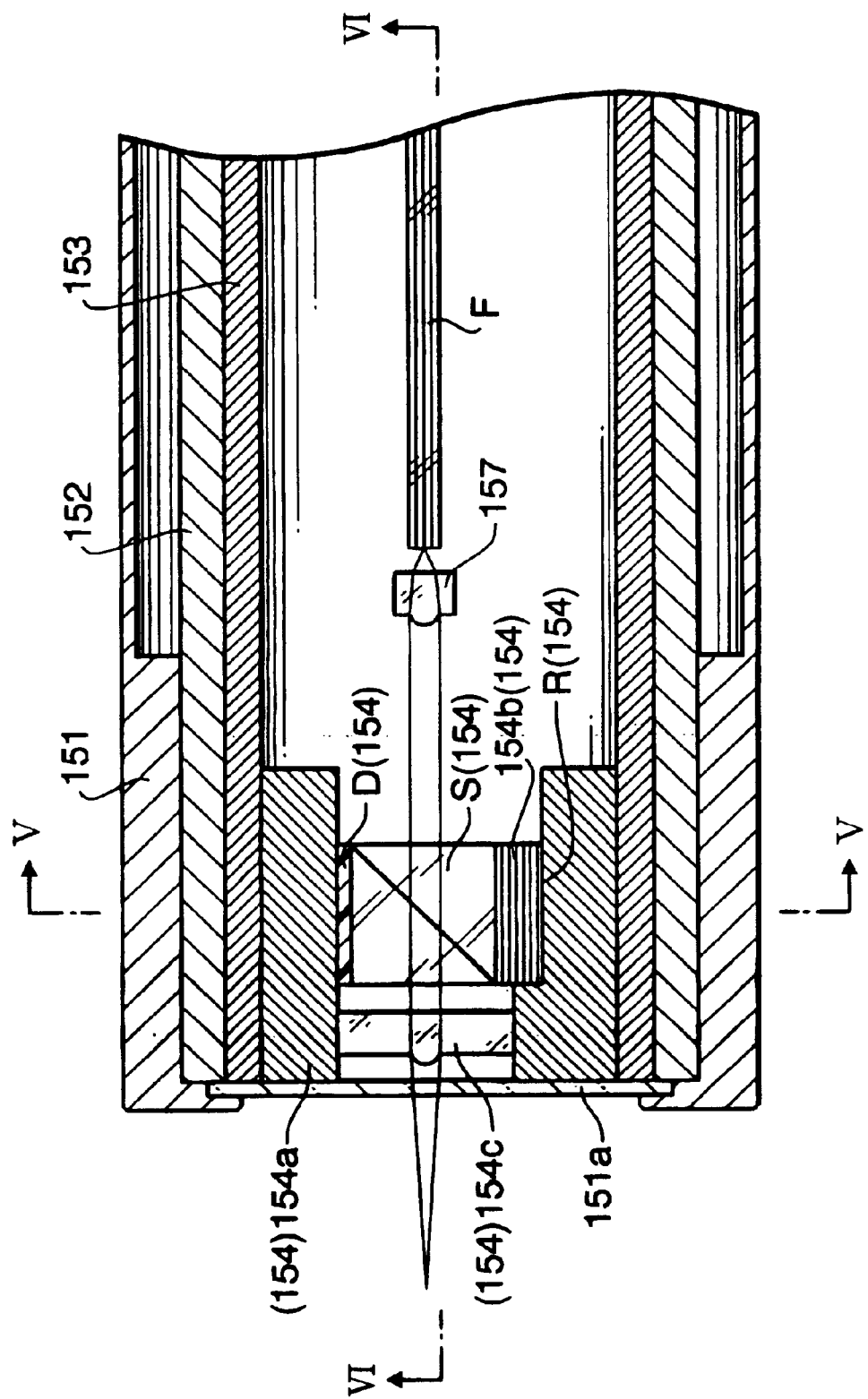
FIG. 4 is cross sectional side view of a distal end of an endoscope according to the embodiment of the invention.
Figure 6:
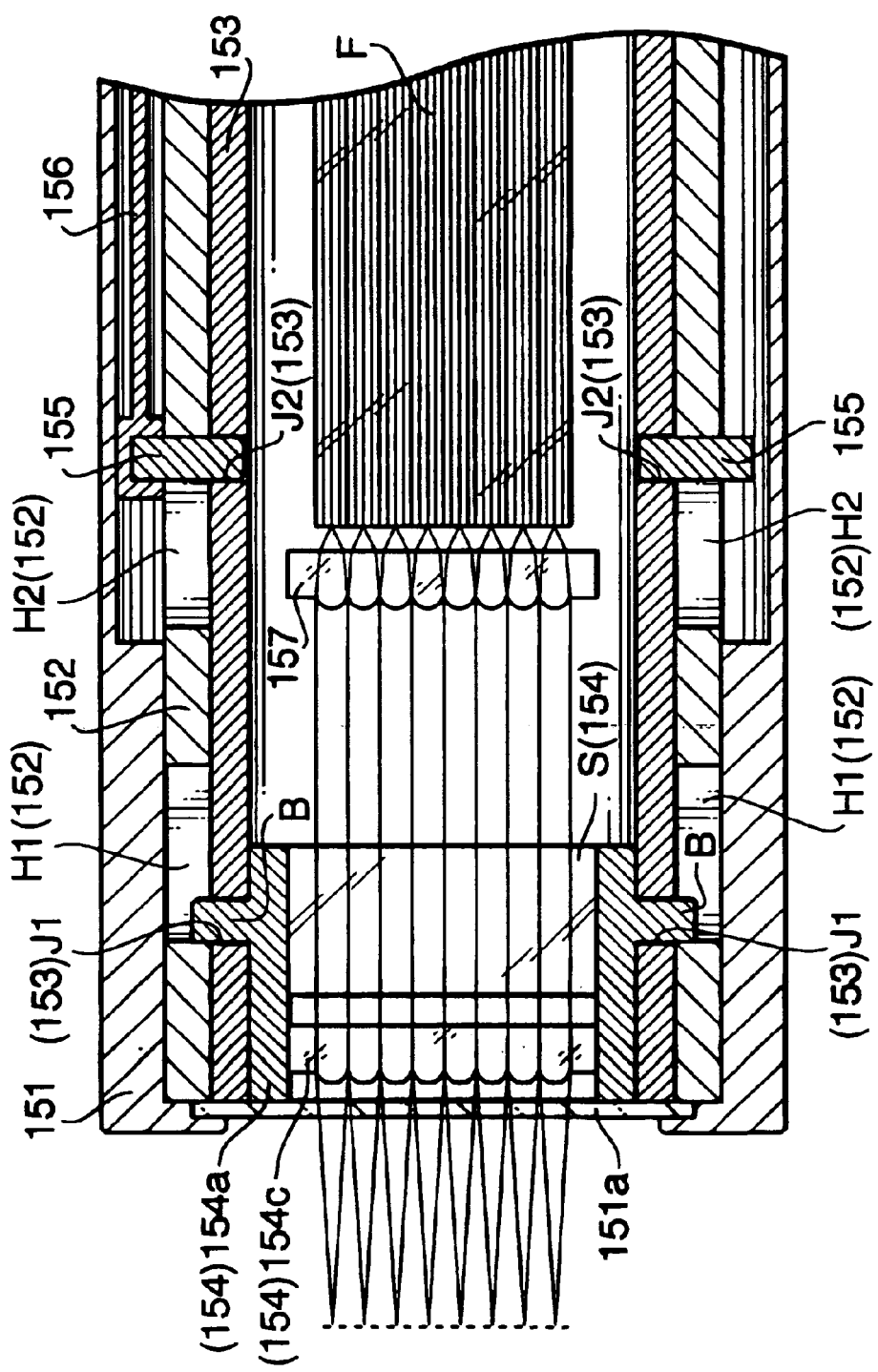
FIG. 6 is a cross section view of the distal end of an endoscope taken along line VI—VI of FIG. 4.
Figure 7:
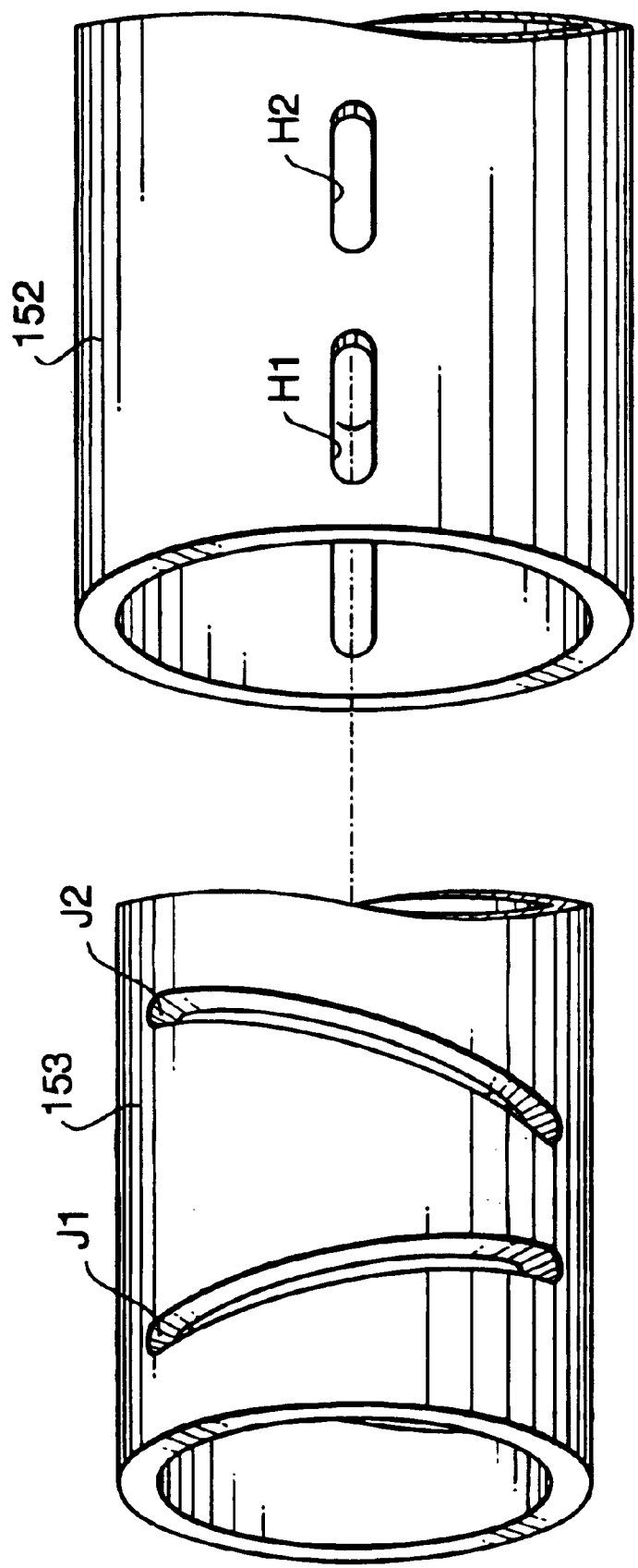
Figure 8:
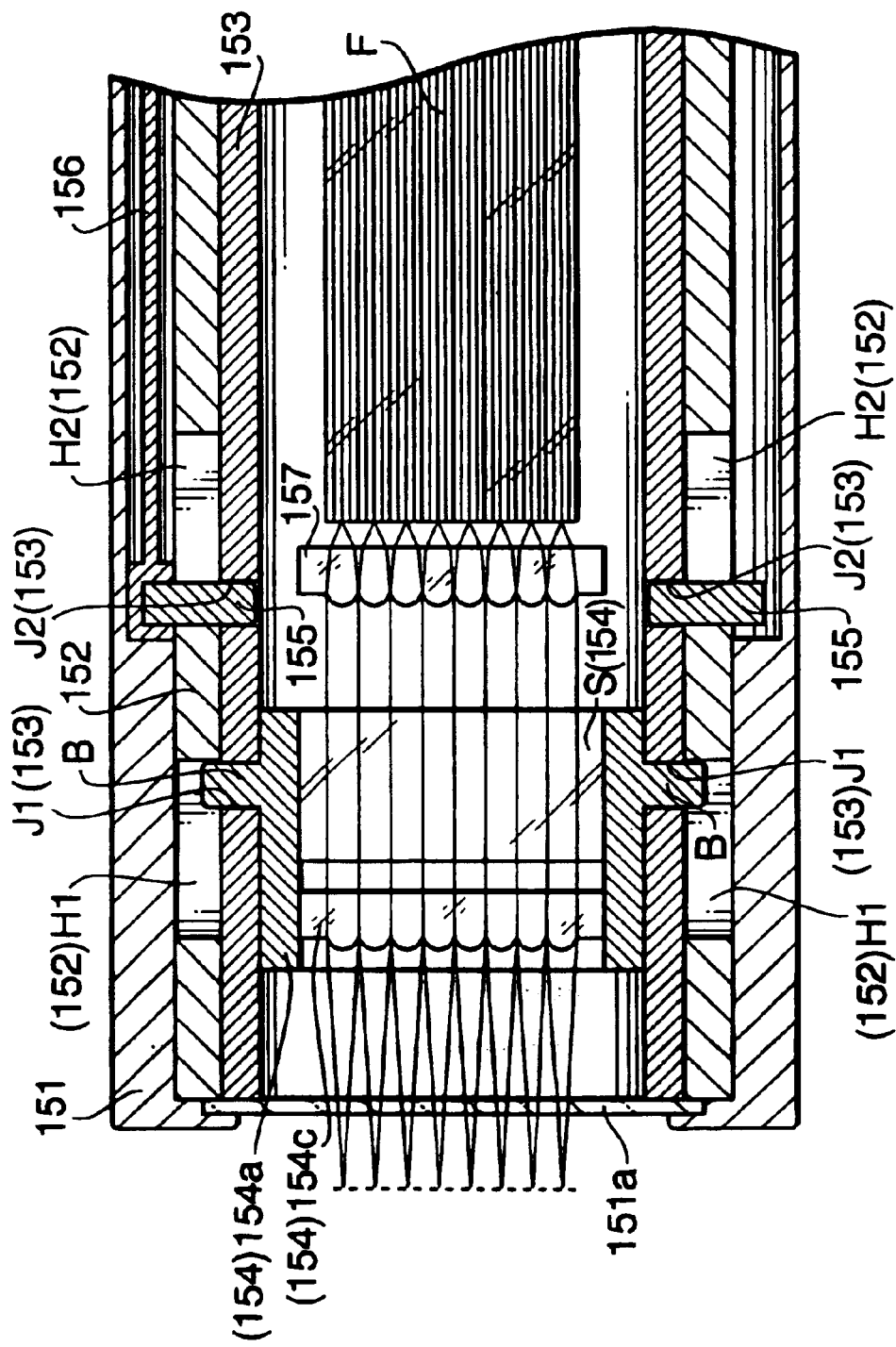
Figure 9A:
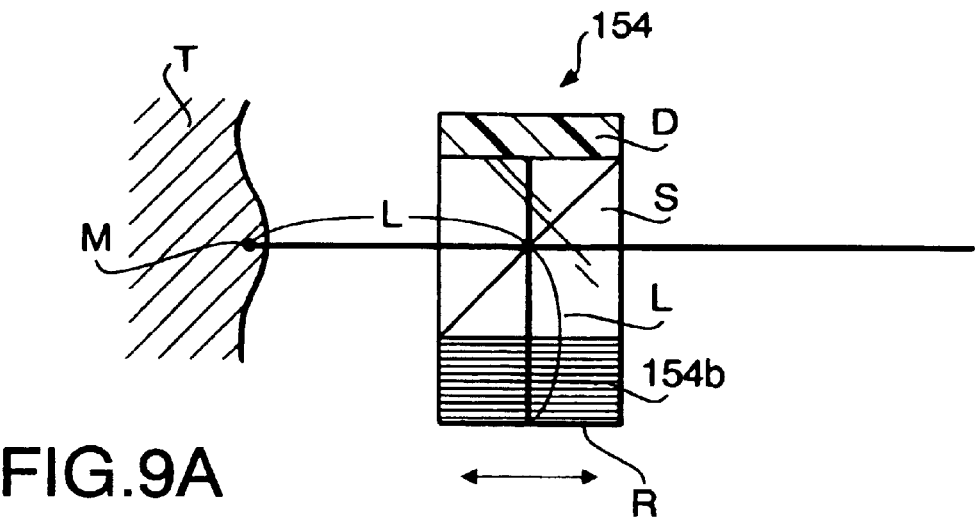
Figure 9B:
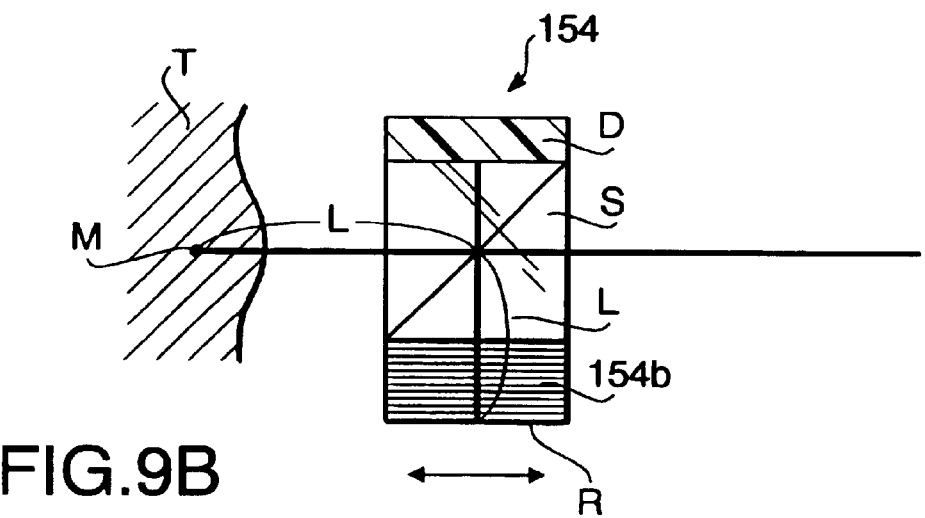
Figure 9C:
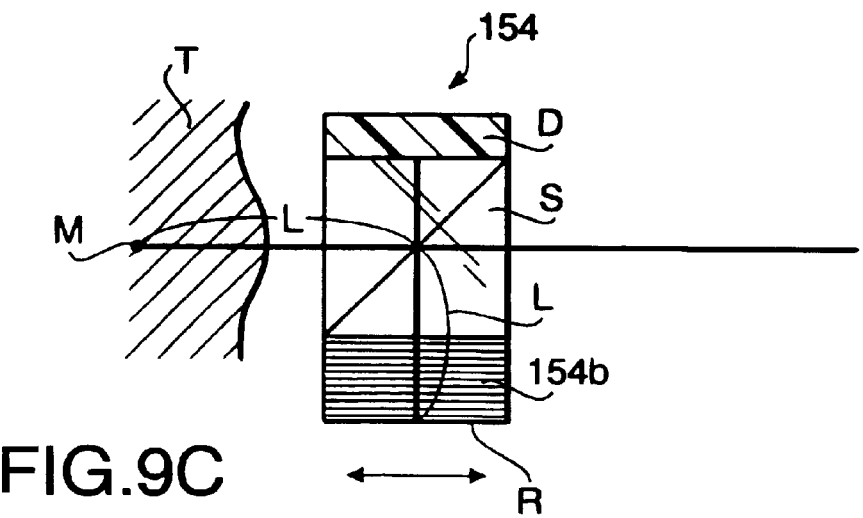

FIG. 7A schematically shows a structure of a first cam ring on which cam slots are pierced;

FIG. 7B schematically shows a structure of a second cam ring on which cam slots are pierced;

FIG. 8 is a cross sectional view of the distal end of an endoscope taken along line VI—VI of FIG. 4, an interferometer unit of the OCT unit being located closer to the distal end than the interferometer unit shown in FIG. 6;

FIG. 9A schematically shows the interferometer unit scanning the object in a direction of depth of the object;

FIG. 9B schematically shows the interferometer unit scanning the object, the interferometer unit being located closer to the object than the interferometer shown in FIG. 9A: and FIG. 9C schematically shows the interferometer unit scanning the object, the interferometer unit being located closer to the object than the interferometer shown in FIG. 9B.

DESCRIPTION OF THE EMBODIMENT

Figure 1:
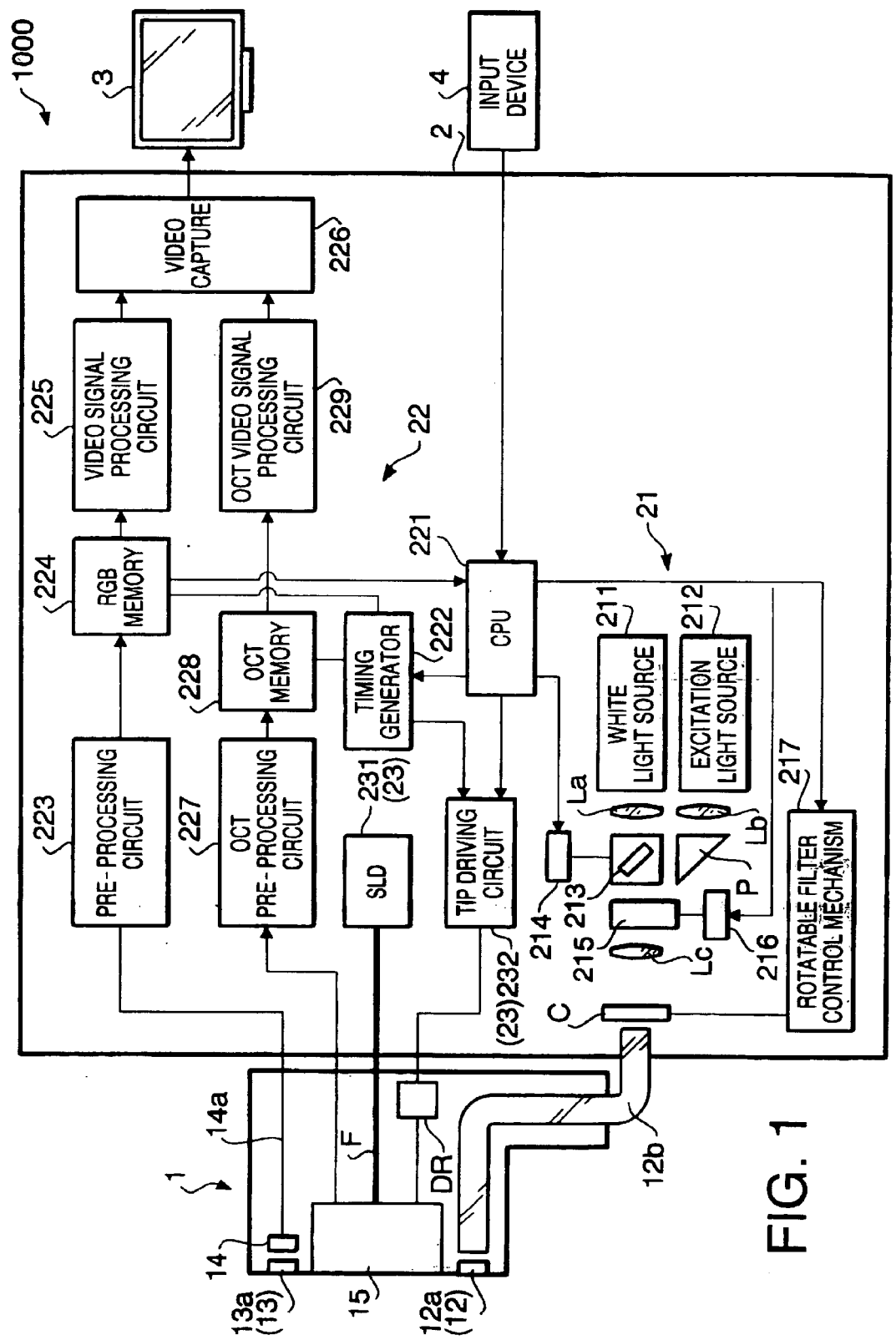

FIG. 1 shows an electronic structure of the endoscope system 1000 according to an embodiment of the invention.

As shown in FIG. 1, the endoscope system 1000 includes an endoscope 1, and external device 2 connected to the endoscope 1, a monitor 3 connected to the external device 2, and an input device 4.

The endoscope 1 includes an insertion tube having an elliptical cross section, and an operation unit which is connected to a proximal end of the insertion tube. Various operation switches are provided on the operation unit.

Inside the insertion tube of the endoscope 1, an illuminating optical system 12, an objective optical system 13, an image capturing system (e.g., CCD: charge coupled device) 14, and an OCT unit 15 are provided. The illuminating optical system 12 is provided with an illumination lens 12a secured at the tip end of the insertion tube, and a light guide fiber bundle 12b (hereinafter referred to as a light guide). The light guide 12b is inserted through the endoscope 1 and connected to the external device 2.

An objective optical system 13 is provided with an objective lens 13a secured at the tip end of the insertion tube, and a cut-off filter, which shields a UV component of the incident light. The objective optical system 13 converges the incident light on the image receiving surface of the CCD 14 and forms an object image thereon. The CCD 14 outputs an image signal corresponding to the optical image formed on the image receiving surface thereof. The CCD 14 is connected to the external device 2 through a signal line 14a, and the image signal is transmitted to the external device 2.

The structure of the OCT unit 15 will be described in detail with reference to FIG. 2 later.

The endoscope 1 constructed as above is connected to the external device 2. The external device 2 will be described in detail hereinafter. As shown in FIG. 1, the external device 2 is provided with a light source unit 21, an image processing unit 22 and an OCT driving unit 23.

The light source unit 21 includes a white light source 211, which emits so-called white light, and an excitation light source 212 which emits excitation light for exciting the human tissues to fluoresce. The wavelength of the excitation light is approximately 350 nm through 400 nm, that is, the excitation light is in a range between so-called blue light and UV (ultraviolet)-light. The wavelength of the fluorescent light, which is emitted from the human tissues upon incidence of the excitation light, is approximately 420 nm through 600 nm.

On an optical path of the white light emitted by the white light source 211, a collimating lens La, a switching mirror 213, an aperture stop 215, a condenser lens Lc, and a rotating filter Care arranged in this order. The switching mirror 213 is connected to a light source switching mechanism 214. Specifically, the light source switching mechanism 214 locates the switching mirror 213 at a retracted position, at which the switching mirror is retracted from the optical path of the white light, or an operable position at which the switching mirror shields the white light (i.e., the switching mirror prevents the white light from proceeding to the aperture stop).

The aperture stop 215 is connected to an aperture control mechanism 216. The aperture stop 215 is controlled by the aperture control mechanism 216 to change the aperture size so as to change the amount of light passed therethrough. The rotatable filter C has a disk like appearance and formed with four fan-shaped filters: RGB color filters (three color filters for red, green and blue components); and a transparent filter. The rotatable filter C is connected to the rotatable filter control mechanism 217. The rotatable filter C is driven by the rotatable filter control mechanism 217 to rotate such that the four filters are sequentially located on an optical path.

The white light emitted by the white light source 211 is collimated by the collimating lens La. If the switching mirror 213 is located at the retracted position, the white light is directed to the aperture stop 215. The white light, light amount of which is adjusted by the aperture stop 215, is converged by the condenser lens Lc, and passes through the rotatable filter C. As described above, the rotatable filter C is rotated by the rotatable filter control mechanism 217 to rotate and the four color filters are sequentially inserted in the optical path. Accordingly, the white light is converted into Blue, Green, Red and white light sequentially, and converged on the proximal end surface of the light guide 12b.

On the optical path of the excitation light emitted by the excitation light source 212, the collimating lens Lb and a prism P are arranged in this order. The excitation light emitted by the excitation light source 212 is collimated by the collimating lens Lb, reflected by the prism P and is directed to the switching mirror 213. If the switching mirror 213 is located at the operative position (as shown in FIG. 1), it reflects the excitation light toward the aperture stop 215. The excitation light, whose light amount is adjusted by the aperture stop 215, is converged by the condenser lens Lc and is directed to the rotatable filter C. In this case, the rotatable filter control mechanism 217 inserts the transparent filter in the optical path and stops rotating the rotatable filter C. Then, the excitation light passes through the transparent filter of the rotatable filter C and is converged on the proximal end surface of the light guide 12b.

Thus, the retracted and operative positions of the switching mirror 213 will be referred to as a normal image observation condition, in which the white light emitted by the white light source 211 is directed to the aperture stop 215, and a fluorescent image observation condition, in which the excitation light emitted by the excitation light source 212 is directed to the aperture stop 215. The rotatable filter C rotates to sequentially insert the filters in the optical path so that, in the normal observation condition, the incident white light is converted into blue, green, red and white light. In the fluorescent image observation condition, the transparent filter is fixedly inserted in the optical path.

Next, the image processing unit 22 will be described. The image processing unit 22 includes a CPU 221 and a timing generator 222. The CPU 221 is connected with the light source switching mechanism 214, the aperture control mechanism 216, and the rotatable filter control mechanism 217 of the light source unit 21, the timing generator 222, and the input device 4. The timing generator 222 generates various reference clock signals. Various processing performed by the image processing unit 22 and various operations performed by the OCT driving unit 23 are executed in accordance with the reference clocks generated by the timing generator 222.

The CPU 221 controls the light source switching mechanism 214 to switch the switching mirror 213 between the normal observation condition and the fluorescent image observation condition, and controls the rotatable filter control mechanism 217 to set the rotatable filter C to the normal image observation condition or the fluorescent image observation condition. Specifically, a switch for selecting the normal image observation and the fluorescent image observation is provided on an operation unit of the endoscope 1. The CPU 221 detects the operation status of the selecting switch, controls the light source switching mechanism 214 and the rotatable filter control mechanism 217 so that the switching mirror 213 and the rotatable filter C are set to one of the normal image observation condition and the fluorescent image observation condition selected by the selecting switch.

The CPU 221, on the other hand, controls the operations executed by the image processing unit 22 and the operations executed by the OCT driving unit 23 via the timing generator 222.

Further, the image processing unit 22 is provided with a pre-processing circuit 223 connected to the CCD 14 through the signal line, an RGB memory 224, a video signal processing circuit 225 and a video capture 226 connected to the monitor 3.

When the switching mirror 213 and the rotatable filter C are set to the normal image observation condition, the pre-processing circuit 223 retains image signals output by the CCD 14 when the blue, green and red components of light are emitted from the illuminating lens 12a, and discards the image signal when the white light is emitted by the illuminating lens 12a. The pre-processing circuit 223 retains the image signals transmitted from the CCD 14, processes the image signals, applies A/D (analog-to-digital) conversion, and stores the digital image signals in the RGB memory 224. It should be noted the blue, green and red components of the image data are stored in the blue, green and red image areas of the RGB memory 224, respectively.

When the switching mirror 213 and the rotatable filter C are set to the fluorescent image observation setting, the pre-processing circuit 223 retains the image signal transmitted by the CCD 14, processes the image signal, applies the A/D conversion, and stores the digital image signal in the all component areas of the RGB memory 224, simultaneously (i.e., processed as monochrome image).

The video signal processing circuit 225 retrieves the data stored in the RGB memory 224 at a predetermined timing and processes the same to generate a video signal, which is transmitted to the video capture 226. The video capture 226 displays the obtained video signal on the monitor 3.

Furthermore, each of the pre-processing circuit 223, the RGB memory 224, and the video signal processing circuit 225 is connected to the timing generator 222. The RGB memory 224 is connected to the CPU 221. Thus, the CPU 221 can control the aperture control mechanism 216 for changing the size of the opening of the aperture stop 215.

The image processing unit 22 further includes an OCT pre-processing circuit 227 connected to the OCT unit 15 of the endoscope 1, an OCT memory 228, and an OCT video signal processing circuit 229. The OCT pre-processing circuit 227 processes the signal transmitted from the OCT unit 15 of the endoscope 1, applies the A/D conversion, and stores the data in the OCT memory 228. The OCT video signal processing circuit 229 retrieves the data stored in the OCT memory 228 at a predetermined timing to generate a video signal, which is transmitted to the video capture 226. The video-capture 226 displays the obtained video signal on the monitor 3. Each of the OCT pre-processing circuit 227, the OCT memory 228, and the OCT video signal processing circuit 229 is connected to the timing generator 222.

Hereinafter, the OCT driving unit 23 will be described in detail. The OCT driving unit 23 comprises a superluminescent diode (SLD) 231, a fiber array F, and a tip driving circuit 232. It should be noted that the OCT driving unit 23 and OCT unit of the endoscope 1 are arranged as described above to form the Michelson interferometer, so as to capture images of paries is of the cavity of a living organization, by applying OCT (Optical Coherence Tomography).

The fiber array F is formed by arranging several hundreds of single-mode optical fibers in parallel. Optionally, each; single-mode optical fibers may be configured to preserve its polarization. The SLD 231 is a light source emitting near-infrared low-coherent light beams. The coherence length of the light beams emitted by the SLD 231 is extremely short, e.g., at the order of 10–1000 micrometers. The SLD 231 is formed as a multi-channel (for instance, several hundreds of channels) system. The low-coherent light beams emitted by the SLD 231 are incident on the optical fibers of the fiber array F respectively and simultaneously.

The tip driving circuit 232 is connected to each of the CPU 221, the timing generator 222, and the OCT unit 15 of the endoscope 1. The tip driving circuit 232, which will be described later, is used for driving an interferometer unit 154 of the OCT unit 15 of the endoscope 1.

Figure 2:
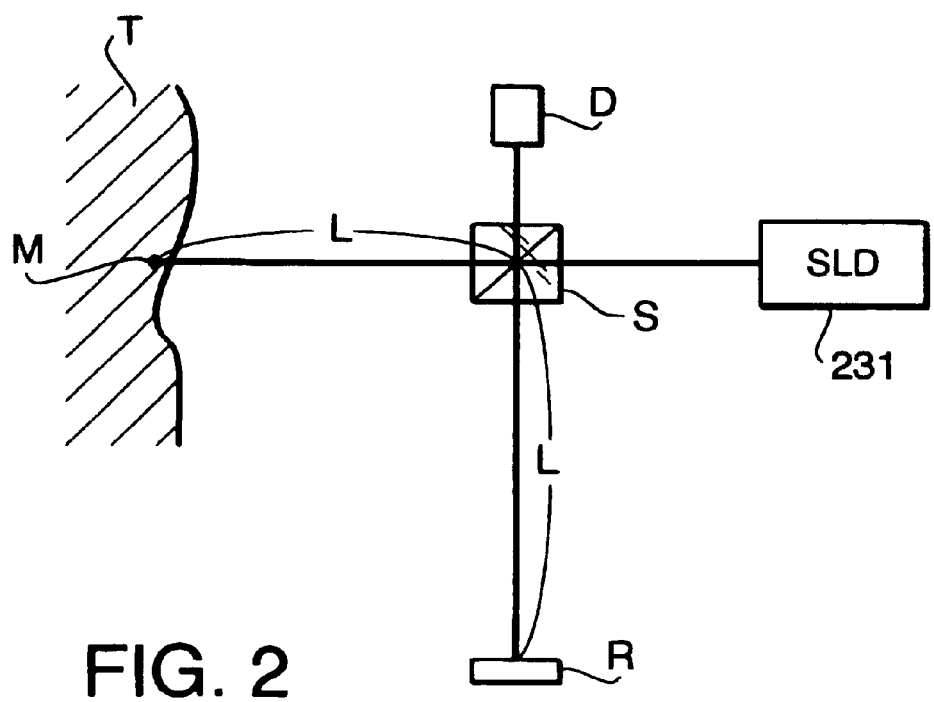

FIG. 2 schematically illustrates the Michelson interferometer constituted by the OCT unit 15 of the endoscope 1 and the OCT driving unit 23 of the external device 2. The principle of capturing tomograms will be described below with reference to FIG. 2. In other to simplify the description, each of the OCT unit 15 and the OCT driving unit 23 is described as a one-channel system in the following description of the principle of the OCT. However, the actual endoscope system according to the invention is a multi-channel system, with which hundreds of points on the object can be observed simultaneously.

The OCT unit 15 is provided with a light detector D, a beam splitter S, and a reflector R. The beam splitter S is arranged on the optical path of the low-coherent light beam in order to split the low-coherent light into two. That is, the low-coherent, light beam incident on the beam splitter S is split into a beam advancing straight through the beam splitter S, and a beam reflected, at right angles, by the beam splitter S. The reflector R is arranged in the optical path of the beam reflected by the beam splitter S.

A value L is defined as an optical path length from the beam splitter S to the reflector R, and an observational point M is defined as a point located on the optical path of the beam advancing straight through the beam splitter S, and spaced from the beam splitter S by distance L. Further, it is assumed that the observational point M is inside an object T which is an tissue of living organization.

In this condition, a low-coherent light beam emitted from the SLD 231 is split into two beams by the beam splitter S. Then, one of the split beams passed through the beam splitter S reaches the object T. The other beam, which is reflected by the beam splitter S, advances toward the reflector R.

The beam which has reached the object T is reflected at a surface of the object T and tissues having various depths from the surface of the object T. Then, the reflected beams, which will be referred to as observational beams, proceed toward the beam splitter S. On the other hand, the beam which has reached the reflector is reflected by the reflector R, and proceeds toward the beam splitter S as a reference beam.

The observational beams and the reference beam interfere at the beam splitter S. Because each of the observational beams is reflected at each position having various depths in the tissues from the object T, the timings at which the observational beams are incident on the beam splitter S spread in some degree. That is, an observational beam reflected on the surface of the object T reaches the beam splitter S first, and the other observational beams reflected at the deeper portions from the surface delay depending on depths thereof.

Meanwhile, since the reference beam is reflected by the reflector R, the timing at which the reflected reference beam(s) do not substantially vary. Thus, only an observational beam whose optical path length is L interferes with the reference beam at the beam splitter S. That is, only the observational beam being reflected at the observational point M interferes with the reference beam at the beam splitter S.

Then, the beams interfering at the beam splitter S (i.e., interfering beams) reach the light detector D, which detects the beams as a signal. The observational beams which do not interfere with the reference beam are also detected by the light detector. The non-interfering beams-are detected, however, as noise components at low signal level.

Figure 3:
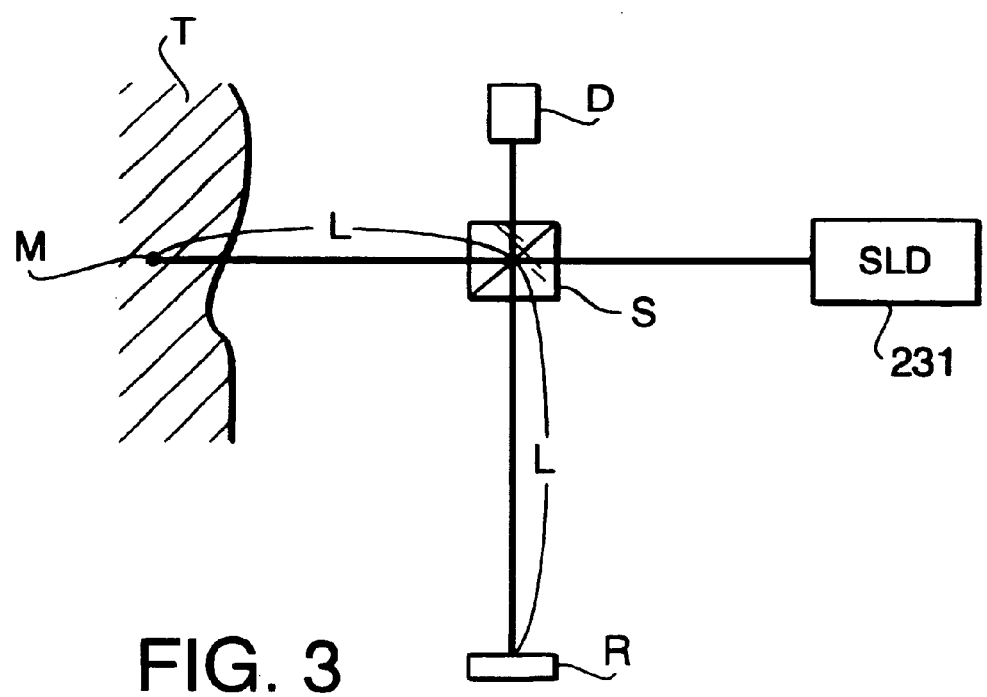

According to the method described above, the intensity of the beam reflected at the observational point M, which is located in the object T, is detected. When the interferometer including the light detector D, the beam splitter S and the reflector R is moved closer to/away from the object T, the observational point M moves accordingly. That is, when the interferometer is located closer to the object T, the observational point M moves deeper from the surface of the object T. FIG. 3 shows such a situation where the interferometer is located closer to the object T with respect to the position thereof shown in FIG. 2. When the interferometer is located farther from the object T, the observational point M moves closer to the surface of the object T.

By moving the interferometer toward/away from the object T, as described above, the object T is scanned along the direction of the depth of the object T. The intensity of the beam reflected at the observational point M varies depending on the condition of the tissue of the object T at the observational point M. Therefore the tomogram is captured based on the intensity distribution of the beams reflected at various locations of the observational point M, from the surface of the object T to a point having a predetermined depth from the surf ace of the object T.

Figure 5:
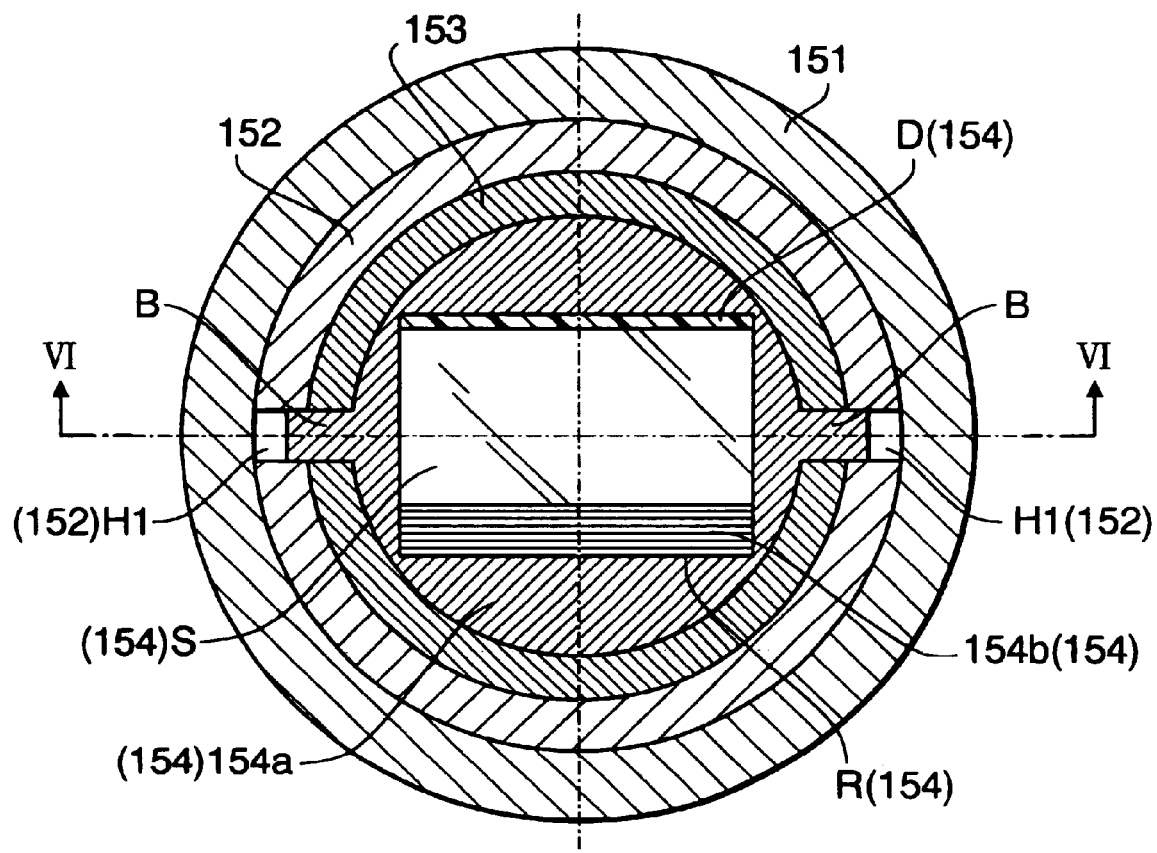
FIG. 5 is a cross sectional view of the distal end of an endoscope taken along line V—V of FIG. 4.

The foregoing describes the principle of the OCT method employed in the endoscope system according to the embodiment. Hereinafter, the actual configuration of the OCT unit 15 will be described with reference to FIGS. 4, 5, 6, 7A, 7B and 8. FIG. 4 is an axial sectional view of the insertion tube of the endoscope 1. FIG. 5 is a cross sectional view taken along line V—V shown in FIG. 4. FIG. 6 is also a cross sectional view taken along line VI—VI shown in FIG. 4 and FIG. 5. As shown in the drawings, the OCT unit 15 has a substantially cylindrical outer tube 151, a first cam ring 152, a second cam ring 153, and an interferometer unit 154. Each of the first and second cam rings 152 and 153, and the interferometer unit 154 is accommodated in the outer tube 151.

Distal end face of the outer tube 151 protrudes inward to form an inner flange. The outer tube 151 is formed such that the distal end portion is relatively thick, and the remaining portion, i.e., on the proximal end side therefrom, is formed thinner. The opening of the outer tube 151 at its distal end is sealed with a disk-shaped cover glass 151a. That is, the cover glass 151a is in intimate contact to the inner flange at the distal end of the outer tube 151 from inside thereof.

The first cam ring 152 is cylindrically formed, and the outer surface of the first camring 152 can be internally contacted with the inner surface of the outer tube 151 at the distal end is portion where it is formed relatively thicker. The second cam ring 153 is cylindrically formed, and the outer surface of the second cam ring 153 can be internally contacted with the inner surface of the first cam ring 152.

Furthermore, on the first cam ring 152, two pairs of cam slots H1 and H2 are formed. On the second cam ring 153, two pairs of cam slots J1 and J2 are formed. The cam slots H1, H2, J1 and J2 will be described hereinafter with reference to FIG. 7A and FIG. 7B.

On the side surface of the first cam ring 152, as shown in FIG. 7A, the cam slot H1 and the cam slot H2 are pierced such that each pair of the cam slots H1 and H2 are elongated along a line parallel to the central axis of the first cam ring 152. The shapes of the slots H1 and slots H2 are substantially the same. The slots H1 are formed at the distal end side of the first cam ring 152, and the slots H2 are formed at the proximal end side. The two pairs of the cam slots H1 and H2 are arranged symmetrically with respect the central axis of the first cam ring 152

On the side surface of the second cam ring 153, as shown in FIG. 7B, a pair of the helical cam slots J1 and J2 are pierced. The cam slot J1 is elongated at a predetermined angle with respect to the central axis of the second cam ring 153, with its one end (top end in FIG. 7B) located on the distal end side (left-hand side in FIG. 7B) of the second cam ring 153, and the other end (lower end in FIG. 7B), which is substantially a half of the circumference away from the one end, located on the proximal end side (right-hand side in FIG. 7B) on the second cam ring 153.

The cam slot J2 is formed on the proximal end side with respect to the cam slot J1. The cam slot J2 is also elongated at a predetermined angle with respect to the central axis of the second cam ring 153, with its one end (top end in FIG. 7B) located on the proximal end side (right-hand side in FIG. 7B), and the other end (lower end in FIG. 7B), which is substantially a half of the circumference away from the one end, is located on the distal end side (left-hand side in FIG. 7B) on the second cam ring 153.

Further, another pair of cam slots, which are similar to the cam slots J1 and J2 described above and rotationally symmetrical to the cam slots J1 and J2, with respect to the central axis of the cam ring 153

When the second cam ring 153 is inserted in the first cam ring 152 such that the distal end of the cam slot H1 coincides with the one end (the upper end in FIG. 7B) of the cam slot J1, the distal ends of the cam rings 152 and 153 coincide with each other. At this stage, the proximal end of the cam slot H2 coincides with the one end (the top end in FIG. 7B) of the cam slot J2.

With this condition, if the second cam ring 153 is rotated substantially half a round with respect to the first cam ring 152 counterclockwise, when viewed from the distal end (i.e., from the left-hand side in FIG. 7B), the proximal end of the cam slot H1 coincides with the-opposite end (i.e., the lower end in FIG. 7B) of the cam slot J1, and the distal end of the cam slot H2 coincides with the opposite end (i.e., the lower end in FIG. 7B) of the cam slot J2.

On the inner surface of the second cam ring 153, the outer surface of which internally contacts the inner surface of the first cam ring 152, the interferometer unit 154 contacts internally. The interferometer unit 154 includes, as shown in FIGS. 4–6, a holding tube 154a, the light detector D, the beam splitter S, a GI (graded index) plate 154b, and a collective lens array 154c.

The outer circumferential surface of the holding tube 154a is formed to-be a substantially cylindrical shape, which is capable of internally contacting the inner surface of the second cam ring 153. Inside the holding tube 154a, a space, a cross section of which is rectangular, is formed. A distal end side portion of the holding tube 154a is formed narrower, in the up/down direction in FIG. 4, than the proximal side portion thereof. In the space, the collective lens array 154c is held at the distal end side portion, while the light detector D, the beam splitter S, and the GI plate 154b are held as a unified part at the intermediate portion of the space. The shape of the collective lens array 154c is substantially a parallel plate, with a plurality of lens surfaces protruded from one surface in correspondence with the plurality of optical fibers of the fiber array F, respectively. Each lens surface of the collective lens array 154c is a rotationally symmetrical convex lens surface. The collective lens array 154c is arranged in the holding tube 154a, such that the optical axis of each lens is parallel with the central axis of the holding tube 154a, and each lens surface faces the distal end side.

The beam splitter S is composed of a pair of right-angle prisms, each of which is formed as an elongated triangular prism. On a sloping surface of one of the right-angle prisms, a semi-permeable membrane is formed, and the pair of the right-angle prisms are cemented at the sloping surfaces thereof.

On one rectangular surface of the beam splitter S, the light detector D is coupled. The light detector D includes a line sensor. On the opposite side surface of the beam splitter S, the GI plate 154b is coupled. The refractive index of the GI plate 154b, at the portion closer to the beam splitter S, is closer to the refractive index that the beam splitter has, and the refractive index of the GI plate 154b is higher at a portion farther from the beam splitters. Furthermore, on the surface of the GI plate, opposite to the surface coupled to the beam splitter S, a reflecting surface R is formed.

The light detector D, the beam splitter S, and the GI plate 154b are held in the space defined inside the holding tube 154a, the inner surface of the holding tube 154a contacting the light detector D and the GI plate 154b.

Furthermore, the holding tube 154a has a pair of cylindrical projections B and B as shown in FIG. 5. the projections are formed symmetrically with each other with respect to the central axis of the holding tube 154a. The holding tube 154a is inserted in the second cam ring 153, with the projections B and B being inserted through the cam slots J1 of the second cam ring 153 and the cam slots H1 of the first cam ring 152.

As described above, the second cam ring 153 and the first cam ring 152 in which the interferometer unit 154 is accommodated are held in the outer tube 151, with the distal ends thereof being contacted against the cover glass 151a.

At the crossing points where the cam slots H2 and H2 and the cam slots J2 and J2 intersect, the pins 155 and 155 are inserted. An arm 156 is connected for transmitting force to one of the pins 155 and 155. The proximal end of the arm 156 is connected to a power unit DR (see FIG. 1), which includes gears and a motor (not shown). The power unit DR is connected to the tip driving circuit 232 of the external device 2. The tip driving circuit 232 can rotate the motor of the power unit DR by supplying electrical current thereto. The rotation of the motor is transmitted to the gears, which drive the arm 156 to move the arm 156 in a direction parallel to the central axis of the outer tube 151. When the arm 156 is located at the most proximal end side, the pins 155 and 155 contact the proximal ends of the cam slots H2 and H2 of the first cam ring 152, and one ends of the cam slots J2 and J2 of the second cam ring 153, respectively. At this stage, the projections B and B of the interferometer unit 154 contact the distal ends of the cam slots H1 and H1 of the first cam ring 152, and one ends of the cam slots J1 and J1 of the second cam ring 153, respectively. In this condition, as shown in FIG. 6, the interferometer 154 is located at the most distal end side position, and, at this stage, the distal end of the holding tube 154a of the interferometer unit 154 contacts the cover glass 151a.

From above condition, if the arm 156 moves toward the distal end side, each of the pins 155 and 155 moves toward the distal end side of the cam slots H2 and H2, with being guided by each of the cam slots H2 and H2. With this movement, the pins 155 and 155 push the cam slots J2 and J2 toward the distal end side, respectively. Thus, the second cam ring 153 is rotated (counterclockwise in FIG. 5). When the second cam ring 153 rotates as described above, the cam slots J1 and J1 push the projections B and B of the interferometer unit 154 toward the proximal end side, respectively. Thus, the interferometer unit 154 moves toward the proximal end side as the projections B and B are guided by the cam slots H1 and H1 of the first cam ring 152.

Then, when the pins 155 and 155 touch the ends of the cam slots H2 and H2 of the first cam ring 152, respectively, the pins 155 and 155 touch the other ends of the cam slots J2 and J2 of the second cam ring 153, respectively. With this movement, the projections B and B of the interferometer unit 154 touch the proximal ends of the cam slots H1 and H1 of the first cam ring 152, and the other ends of each of the cam slots J1 and J1 of the second cam ring 153, respectively. At this stage, as shown in FIG. 8, the interferometer unit 154 is located at the most proximal end side.

On the contrary, from the condition shown in FIG. 8, if the arm 156 moves toward the proximal end of the outer tube 151, the pins 155 and 155 move toward the proximal end side of the cam slots H2 and H2, with being guided by the cam slots H2 and H2. At this stage, the pins 155 and 155 push the cam slots J2 and J2 toward the proximal end. Thus, the second cam ring 153 is rotated (clockwise in FIG. 5). As the second cam ring 153 rotates as described above, the cam slots J1 and J1 push the projections B and B of the interferomreter unit 154 toward the distal end. Thus, the interferometer unit 154 moves toward the distal end side by the cam slots H1 and H1 of the first cam ring 152, with being guided by the projections B and B. Then, if the arm 156 moves to the most proximal end side position, the interferometer unit 154 is located at the most distal end side position, i.e., back to the position shown in FIG. 6.

That is, when the arm 156 moves from the proximal end side to the distal end side, the interferometer unit 154 moves from the distal end side position to the proximal end side position. When the arm 156 moves from the distal end side to the proximal end side, the interferometer unit 154 moves from the proximal end side position to the distal end side position.

Through the space inside the second cam ring 153 of the OCT unit 15, in the proximal end side portion with respect to the interferometer unit 154, a fiber array F is inserted. The OCT unit 15 has a collimating lens array 157 facing the tip end of the fiber array F. The fiber array F and the collimating lens array 157 are held by a holding member (not shown). The proximal end portion of the holding member is secured on the outer tube 151. Therefore, even if the interferometer unit 154 translates toward the distal end side or the proximal end side as the second cam ring 153 rotates, the fiber array F and the collimating lens array 157 are not displaced with each other with respect to the outer tube 151, cover glass 151a and the first cam ring 152.

The shape of the collimating lens array 157 is substantially a parallel plate, with a plurality of lens surfaces respectively corresponding to the optical fibers of the fiber array F being formed on one surface thereof. The collimating lens array 157 is arranged such that the surface on which the plurality of lens surfaces are formed faces the beam splitter S of the interferometer unit 154, that optical axis of each lens surfaces coincides with the optical axis of each lens surfaces of the collective lens array 154c of the interferometer unit 154, and that the surface on which the plurality of lens surfaces are formed is spaced from the cover glass 151a by a predetermined distance.

The fiber array F is arranged such that the optical axes of the optical fibers coincide with the optical axes of the lens surfaces of the collimating lens array 157, respectively. Further, the fiber array F is arranged to be spaced from the collimating lens array 157 by a predetermined distance. In this condition, the focal points of the lens surfaces of the collimating lens array 157 on the fiber array F side are located on the light emitting end surfaces of the optical fibers of the fiber array F, respectively.

The low coherent beams emitted by the optical fibers of the fiber array F are incident on rear areas of the lens surfaces of the collimating lens array 157. Then, the collimating lens array 157 converts the incident low coherent beams into parallel beams, respectively. That is, each homologous beam emitted by each optical fiber is converted into a parallel light beam. Further, principal rays of the homologous beams respectively emitted by the lens surfaces of the collimating lens array 157 are parallel to each other.

Each of the parallel beams emitted from the collimating lens array 157 is incident on the beam splitter S of the interferometer unit 154. The beam splitter S splits each of parallel beams into two beams, i.e., a beam that advances straight through the beam splitter S, and another beam which is reflected by a reflection surface of the beam splitter S and turns at 90 degree with respect to the incident beam.

The transmitted beams are incident on the collective lens array 154c. Then lens surfaces of the collective lens array 154c converge the incident low-coherent light beams. The low-coherent light beams emitted from the collective lens array 154c are emerged outside of the endoscope 1 through the cover glass 151a, and are converged on an object facing the cover glass 151a.

The low-coherent beams reflected by the surface of the object or layers beneath the object surface (i.e., inside the object) are incident on the collective lens array 154c of the interferometer unit 154 as observational beams. The collective lens array 154c converts the observational beams into parallel beams, which are directed to the beam splitter S.

The reflected beams that are reflected by the beam splitter S are incident on the GI plate 154b, and reflected by the reflecting surface R of the GI plate 154b. The low-coherent beams reflected by the reflecting surface R pass through the GI plate again, and proceed toward the beam splitter S as reference beams.

The observational beams and reference beams interfere with each other to form interfered beams, then the interfered beams are detected by the light detector D, respectively. Because the observational beams are reflected at layers in the tissues constituting the object T at various depths, the timing at which the observational beams are incident on the beam splitter S spreads over some degree. That is, an observational beam reflected on the surface of the object T reaches the beam splitter S earlier than another observational beam reflected at a deeper tissue layer.

On the other hand, the timing at which the reference beams reach the beam splitter does not distribute in a range substantially because the reference beams are reflected on the reflector R. In this regard, only the observational beams whose optical path length is substantially the same as the optical path length of the reference beams converted into the optical path length through air, interfere with the reference beams. It should be noted that the optical paths of the reference beams are in the GI plate having a relatively high refractive index, and therefore, the geometrical optical path length of the observational beams are greater than the geometrical optical path length of the reference beams. With this constitution the optical paths of the reference beams can be provided within a smaller range, while allowing the geometrical length of the optical paths of the observational beams to be sufficiently long.

When the interferometer unit 154 translates toward the distal end or proximal end as the arm 156 moves, a position (observational position M) in the optical paths of the observational beams equivalent to the reflecting surface R in the optical paths of the reference beams moves along with the interferometer unit 154. A method of scanning the object in the depth direction by moving the interferometer 154 will be described below, with reference to FIGS. 9A, 9B and 9C.

As shown in FIG. 9A, the observational point M that is equivalent to the reflecting surface R is located at a relatively shallow position with respect to the surface of the object T. From this condition, if the interferometer unit 154 moves toward the object T, the observational point M moves to a deeper position in the object T, as shown in FIG. 9B. If the interferometer further moves toward the object T, the observational point M moves to a deeper position in the object T, as shown in FIG. 9C.

As described above, if the interferometer unit 154 moves with the endoscope 1 being faced to the object T, the observational point M in the object T moves in the depth direction of the object T. Therefore, the object T can be scanned in the depth direction by moving the interferometer unit 154. The number of the observational points M can be virtually formed as the number of the optical fibers of the fiber array F (i.e., the number of channels). Therefore, the object T is scanned two-dimensionally, in accordance with line segments connecting a plurality of observational points M, and in accordance with the depth thereof.

The operation of the endoscope system constructed as above will be described hereinafter.

When an operator powers ON the external device 2, the white light source 211 and the excitation light source 212 are turned ON. The switching mirror 213 and the rotatable filter C are, at the initial stage, positioned at the normal observation positions. Therefore, the white light emitted by the white light source 211 passes through the aperture stop 215 and is incident on the condenser lens Lc.

The rotatable filter control mechanism 217 sequentially inserts the filters of the rotational filter C. Accordingly, the white light emerged from the condenser lens Lc is changed to Blue, Green, Red and white light sequentially, and then converged on the proximal end side surface of the light guide 12b. The light incident on the light guide 12b is directed thereby and emerged from the illuminating lens 12a. That is, from the illuminating lens 12a, the Blue light, Green light, Red light and the white light are emerged sequentially.

If the operator inserts the insertion tube of the endoscope 1 inside the human cavity, and the illuminating lens 12a of the illuminating optical system 12, and the objective lens 13a of the objective optical system 13 are faced to the paries of the human cavity to be observed, the light emitted from the illuminating lens 12a sequentially illuminates the paries.

Then, the paries is sequentially illuminated by the blue, green, red and white light, images of the corresponding color components are formed on the image receiving surface of the CCD 14 by the objective optical system 13. Then, the CCD 14 converts the optical image into the electric image, and the electrical image (i.e., the image signal) is transmitted to the pre-processing circuit 223. The pre-processing circuit 223 retains the image signals obtained when the blue, green and red light are emitted from the illuminating lens 12a, and the image signal obtained when the white light is emitted is abandoned.

The pre-processing circuit 223 applies signal processing to the retained image signals, and then performs the A/D conversion. The image data (i.e., A/D converted image data) thus obtained is stored to B, G and R areas of the RGB memory 224, in this order. Specifically, the image data obtained when the Blue light is emitted from the illuminating lens 12a is stored in the B area of the RGB memory 224. Similar procedure is performed for the data obtained when the Green light, and the Red light are emitted from the illuminating lens 12a.

The video signal processing circuit 225 retrieves the data stored in the RGB memory 224 at a predetermined timing to generate a color video signal, which is transmitted to a video capture 226. When the video capture 226 receives the video signal, it displays an image corresponding to the received video signal on the monitor 3. At this stage, the operator can observe the surface of the paries of the patient via the monitor 3.

The operator can designate a fluorescent image by operating a switch on the operation unit. Upon operation of the switch, the CPU 221 controls the light source switching mechanism 214 to locate the mirror 213 at the fluorescent image monitoring position, and controls the rotatable filter control mechanism 217 to set the rotatable filter C in the fluorescent image. observing condition. With above control, the white light emitted by the white light source 211 is shielded and the excitation light emitted by the excitation light source 212 is introduced in the light guide 12b. The excitation light introduced in the light guide 12b is emerged from the illuminating lens 12a and illuminates the paries of the body cavity.

The tissues of the surface of the body cavity emits fluorescent light whose wavelength is different from that of the excitation light. It has been known that the fluorescent light emitted by the diseased tissues (i.e., suffered from cancer or a tumor) has less intensity than that emitted by normal tissues.

The fluorescent light emitted by the tissues is incident on the objective optical system 13 together with the reflected excitation light. The objective optical system 13 is provided with a cut off filter which cuts off the excitation light and allows the fluorescent light to pass through. Therefore, the fluorescent light is converged on the image receiving surface of the CCD 14, i.e., an optical image is formed on the image receiving surface of the CCD 14.

The CCD 14 converts the optical image into the image signal, which is transmitted to the pre-processing circuit 223. The pre-processing circuit 223 receives the image signal, applies processing such as amplification and the like, and applies the A/D conversion to generate digital image data. The image data is stored in Blue, Green and Red areas of the RGB memory 224 at the same time. That is, the fluorescent image is treated as a monochromatic image. The video signal processing circuit 225 retrieves the data stored in the RGB memory 224 at a predetermined timing and processes the same to generate a monochromatic video signal, which is transmitted to the video capture 226. The video capture 226 displays a monochrome image in accordance with the received video signal. In the embodiment, the fluorescent image is displayed as a monochromatic image. It can be modified such that the fluorescent image is displayed as a color image. In this case, the color of portions of the image may be determined, for example, based on the intensity of the fluorescent light.

The operator can observe the fluorescing condition of the paries of the cavity through the monitor 3. If there is a portion whose intensity is lower than the other portion, it may be considered as a diseased portion where the cancer or tumor is formed.

When the operator identifies the portion, which may be diseased, by the normal image observation or fluorescent image observation, OCT images of the portion in question will be obtained. That is, when the operator identifies the portion which needs further inspection, the operator may operate the operation unit to select capturing of the tomogram. Then, the CPU 221 controls the OCT driving unit 23 to start capturing tomogram.

Then low-coherent light is emitted from the SLD 231. Further, the tip driving circuit 232 reciprocates the interferometer unit 154 of the OCT unit 15 at a high speed, so that the interferometer unit 154 moves toward/away from the object.

Then, the low-coherent light beams emitted from SLD 231 are guided, by the optical fibers of the fiber array F, toward the distal end. Each low-coherent light beam emitted from the distal end of the fiber array F is split into two beams by the beam splitter S, i.e., a beam that passes through the beam splitter S, advances toward the paries of the human cavity, and is converged on the paries, and another beam that is reflected by the beam splitter S, proceeds through the GI plate 154b, then is reflected by the reflector surface R. The observational beams reflected on the paries and the reference beams reflected by the reflecting surface R interfere with each other in the beam splitter S, then the interfered beams are detected by the detector D.

At this stage, the tip driving circuit 232 of the OCT driving unit 23 drives the interferometer unit 154 to move, and therefore, the observational points M are reciprocated in the depth direction of the object. Thus, a predetermined range of depth (for instance, 2 mm) from the surface of the paries is scanned.

Practically, the scanning in the depth direction starts from a location closer to the endoscope 1 with respect to the surface of the paries. During the scanning, the OCT is pre-processing circuit 227 checks the outputs of all the channels from the detector D, respectively.

In this case, when an observational point M has not reached the surface of the paries, the OCT pre-processing circuit 227 does not detect the signal from the corresponding channel. When the observational point M has reached the surface of the paries, the OCT pre-processing circuit 227 detects the signal from the corresponding channel. Then, the OCT pre-processing circuit 227 does calibration, i.e. a zero-point adjustment by regarding the firstly detected depth as the surface of the paries. That is, the OCT pre-processing circuit 227 recognizes that the depth when the signal is firstly detected is the surface of the paries (0 depth), and holds the signals obtained within a range of a predetermined depth (e.g., 2 mm) therefrom, while abandoning the other signals.

Then, the OCT pre-processing circuit 227 applies signal processing, such as amplification, decoding and A/D conversion to the kept signals. The data thus obtained by the pre-processing circuit 227 is stored in the OCT memory 228. The OCT video signal processing circuit 229 retrieves the data stored in the OCT memory 228 at a predetermined timing and processes the same to generate a video signal, which is transmitted to the video capture 226. The video capture 226 displays an image on the monitor 3 in accordance with the received video signal. Thus, the tomogram from the surface to the predetermined depth is displayed on the monitor 3. Optionally, the video capture 226 is capable of displaying the tomogram as well as the normal image and the fluorescent image on the monitor 3 at the same time, by dividing the displaying area of the monitor 3.

With the above-described configuration, the operator can recognize the condition beneath the paries of the cavity, an accurate and quick diagnosis can be made. Further, by the observation using only the endoscope, the operator can find the early cancer, a small tumor, or the like.

Further, since the accurate and quick diagnosis becomes possible, the operator can perform the necessary treatment of the diseased portion. For example, a forceps, laser treatment instrument or the like can be inserted through the treatment channel of the endoscope, and the treatment of the diseased portion may be performed immediately. In such a case, the burden to the patient is considerably decreased.

Furthermore, since the optical paths for the reference beams are provided in the GI plate 154b, the structure for the reference beams is made compact, with providing a sufficiently long geometric length of the optical paths of the observational beams. Therefore, the interferometer unit 154 can be housed in a limited space of the distal end portion of the endoscope 1. Thus, it becomes unnecessary to incorporate the interferometer unit 154 in the external device 2, which realizes a downsized endoscope system.

The present disclosure relates to the subject matter contained in Japanese Patent Application No. HEI 11-306441, filed on Oct. 28, 1999, which is expressly incorporated herein by reference in its entirety.

What is claimed is:

1. An endoscope system, comprising:
   a light guide including a plurality of optical paths;
   a low-coherent light source that emits low-coherent light beams, said low-coherent light source being provided at a proximal end side of said light guide, the light beams emitted by said low-coherent light source being incident on said plurality of optical paths, respectively;
   an interferometer unit accommodated in an endoscope, including:
      a beam splitting element that splits each of the low-coherent beams emitted from a distal end of said light guide and emits one split beam of each of the low-coherent beams to an object;
      a reference optical system that guides an other split beam of each of the low-coherent beams;
      a reflector unit that reflects the other split beam of each of the low-coherent beams guided by said reference optical system toward said beam splitting element; and
      a light detecting device that detects an interfered beam generated by interference, at said beam splitting element, between a beam reflected by the object and the other split beam reflected by said reflector unit;
   a signal processing system that generates a tomogram based on signals detected by said light detecting device; and
   a driving unit that moves said entire interferometer unit at least one of towards and away from the object relative to the endoscope.

2. The endoscope system according to claim 1, wherein said reference optical system comprises a gradient index optical member whose refractive index is greater at a portion closer to said reflector unit.

3. The endoscope system according to claim 2, wherein the refractive index of said gradient index optical member, at a beam splitting element side, has the same refractive index as said beam splitting element.

4. The endoscope system according to claim 1, wherein said interferometer unit is accommodated in a distal end portion of the endoscope system.

5. The endoscope system according to claim 1, wherein said driving unit includes:
- a driving force supply that is provided at a proximal end side of said endoscope system and supplies a driving force; and
- a force transmitting member that is connected to said driving force supply and said interferometer unit, said force transmitting member transmitting the driving force supplied by said driving force supply and moves said interferometer unit.

6. The endoscope system according to claim 1, wherein said light guide comprises a fiber array having a plurality of single-mode optical fibers arranged in parallel.

7. The endoscope system according to claim 6, further comprising:
- a collimating lens array that is formed with a plurality of lens surfaces that collimate each beam emitted from said fiber array into a parallel light beam, each parallel light beam being directed toward said beam splitting element; and
- a collective lens array including a plurality of lens surfaces that converges one parallel beam split by said beam splitting element on the object.

8. The endoscope system according to claim 1, wherein said low-coherent light source includes a super-luminous diode.

9. The endoscope system according to claim 1, further comprising:
- an illuminating optical system that emits at least one of visible light, and excitation light which causes biotissues to fluoresce, toward the object;
- an objective optical system that converges light from the surface of the object to form an object image; and
- an image capturing system that captures an optical image formed by said objective optical system.

10. The endoscope system according to claim 9, further comprising:
- a visible light source that emits visible light;
- an excitation light source that emits the excitation light; and
- a light source switching system that causes one of the visible light and the excitation light to be incident on said illuminating optical system,
- wherein said objective optical system forms a normal light image of the object when the visible light is incident on said illuminating optical system, and
- wherein said objective optical system forms a fluorescent light image of the object when the excitation light is incident on said illuminating optical system.

11. The endoscope system according to claim 9, further comprising a displaying device that displays the object image captured by said image capturing system, and the tomogram generated by said signal processing system.

* * * * *